US009839725B2

(12) United States Patent
Delaney, Jr. et al.

(10) Patent No.: US 9,839,725 B2
(45) Date of Patent: Dec. 12, 2017

(54) LUBRICIOUS ONE-PART HYDROPHILIC COATINGS

(71) Applicant: BOSTON SCIENTIFIC SCIMED, INC., Maple Grove, MN (US)

(72) Inventors: Joseph Thomas Delaney, Jr., Minneapolis, MN (US); Kasyap Seethamraju, Dunwoody, GA (US); Paul Vincent Grosso, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 98 days.

(21) Appl. No.: 14/820,342

(22) Filed: Aug. 6, 2015

(65) Prior Publication Data
US 2016/0058918 A1 Mar. 3, 2016

Related U.S. Application Data

(60) Provisional application No. 62/042,033, filed on Aug. 26, 2014.

(51) Int. Cl.
*A61F 2/00* (2006.01)
*C08L 75/00* (2006.01)
*B05D 3/00* (2006.01)
*C08F 2/50* (2006.01)
*A61L 31/10* (2006.01)
*A61L 29/08* (2006.01)
*A61L 31/08* (2006.01)
*A61L 31/14* (2006.01)
*C09D 175/04* (2006.01)

(52) U.S. Cl.
CPC .............. *A61L 31/10* (2013.01); *A61L 29/085* (2013.01); *A61L 31/082* (2013.01); *A61L 31/14* (2013.01); *C09D 175/04* (2013.01); *A61L 2400/10* (2013.01); *A61L 2420/02* (2013.01); *A61L 2420/06* (2013.01)

(58) Field of Classification Search
None
See application file for complete search history.

(56) References Cited

U.S. PATENT DOCUMENTS

| 6,096,525 | A | 8/2000 | Patnaik |
| 6,299,980 | B1 | 10/2001 | Shah et al. |
| 7,772,393 | B2 | 8/2010 | Guire et al. |
| 8,133,580 | B2 * | 3/2012 | Dias ................. A61L 29/085 424/422 |
| 8,377,461 | B2 | 2/2013 | Chinn et al. |
| 2004/0121037 | A1 | 6/2004 | Rouns et al. |
| 2007/0128246 | A1 * | 6/2007 | Hossainy ............. A61L 31/10 424/423 |

FOREIGN PATENT DOCUMENTS

| DE | 10053554 A1 | 5/2002 |
| WO | 9311751 A1 | 6/1993 |
| WO | 9858988 A1 | 12/1998 |
| WO | 0062830 A2 | 10/2000 |
| WO | 2011084811 A1 | 7/2011 |

OTHER PUBLICATIONS

Lee et al.; JCT Research, vol. 3, No. 3, Jul. 2006.*
Zhang et al., "Synthesis and Characterization of Heterotelechelic Poly(ethylene glycol)s with Amino Acid at One End and Hydroxyl Group et Another End", Journal of Applied Polymer Science, vol. 110, pp. 2432-2439, 2008.

* cited by examiner

*Primary Examiner* — Jeffrey T Palenik
(74) *Attorney, Agent, or Firm* — Seager, Tufte & Wickhem, LLP

(57) ABSTRACT

A lubricious coating for use on an implantable medical device includes a heterochelic component, a homotelechelic polymer and biocompatible initiator. Methods of forming such lubricious coatings are also provided.

16 Claims, 1 Drawing Sheet

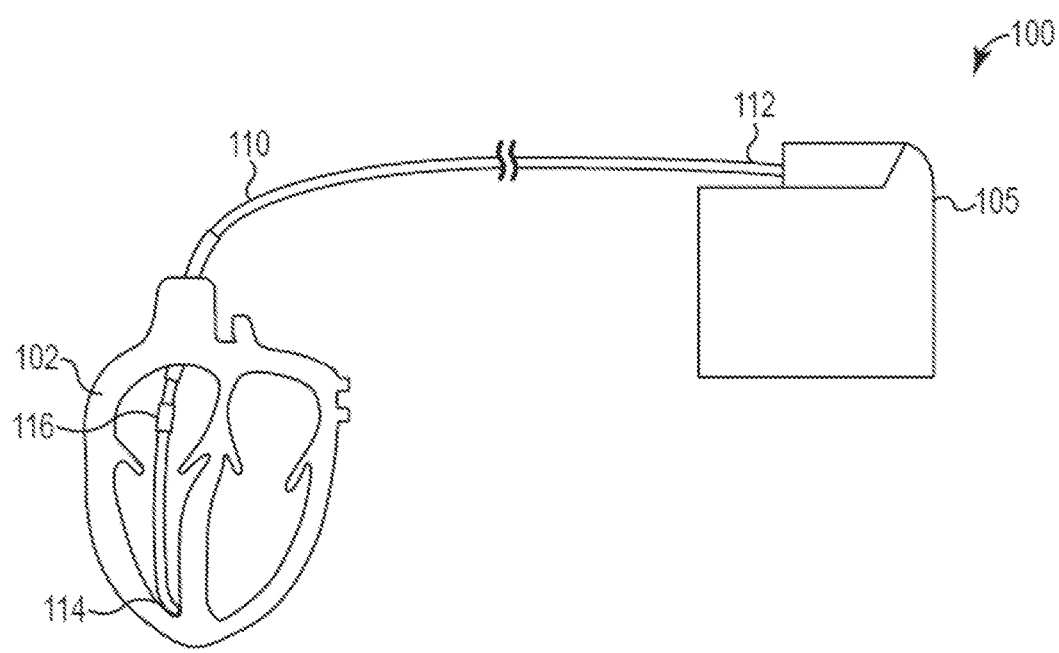

LUBRICIOUS ONE-PART HYDROPHILIC COATINGS

CROSS-REFERENCE TO RELATED APPLICATIONS

This application claims priority under 35 U.S.C. §119 to U.S. Provisional Application Ser. No. 62/042,033, filed Aug. 26, 2014, the entirety of which is incorporated herein by reference.

TECHNICAL FIELD

The present invention relates to lubricious coating for an implantable medical device. More specifically, the invention relates to lubricious one-part hydrophilic coatings and methods of making such coatings.

BACKGROUND

Implantable medical devices can be formed from a number of materials such as metals, including titanium, stainless steel and alloys thereof, and polymeric materials, including polyolefins, polyesters, silicones, polyethers, urethanes and nylons. Selection of such materials for use in implantable medical devices includes consideration of numerous factors including material properties, application of the medical device, and duration of residence in the human body.

In some applications, it can be desirable to modify a surface of the implantable medical device. For example, it may be desirable to modify the surface of the implantable medical device to impart lubricity, antimicrobial action, anti-fouling properties, biocompatibility and/or the release of bioagents such as anticoagulants or growth factors for regulating cell behavior.

In some applications, it may also be desirable that the process of modifying the surface be simple, and preferably a single step or one-step process. It may also be desirable that the surface modification be durable and capable of withstanding mechanical wear caused for example by the medical implantable device rubbing or dragging on surrounding or nearby components and/or environment.

SUMMARY

In Example 1, an implantable medical device includes a body member having a surface, and a coating applied to at least a portion of the surface. The coating includes a heterochelic component having a first reactive group and a second reactive group, the first reactive group reactive with at least a portion of the surface and the second reactive group non-reactive with the portion of the surface with which the first reactive group is reactive, a homotelechelic polymer reactive with the second reactive group of the heterochelic hydrophilic component, and a biocompatible initiator. The heterochelic component is crosslinked with the homotelechelic polymer.

In Example 2, the implantable medical device according Example 1 wherein the heterochelic component is a hydrophilic heterochelic component.

In Example 3, the implantable medical device according to any of the preceding Examples wherein the homotelechelic polymer is a hydrophilic homotelechelic polymer.

In Example 4, the implantable medical device according to any of the preceding Examples wherein the first reactive group is selected from the group consisting of isocyanate, isothiocyanate, orthosilicate esters, and chlorosilicates and combinations thereof.

In Example 5, the implantable medical device according to any of the preceding Examples wherein the coating has a lower coefficient of friction than the surface on which it is applied.

In Example 6, the implantable medical device according to any of the preceding Examples wherein the heterochelic component is aprotic.

In Example 7, the implantable medical device according to any of the preceding Examples wherein the homotelechelic polymer is aprotic.

In Example 8, the implantable medical device according to any of the preceding Examples wherein the biocompatible initiator is selected from the group consisting of biocompatible photoinitiators and biocompatible thermal initiators.

In Example 9, the implantable medical device according to any of the preceding Examples wherein the surface comprises a metal.

In Example 10, the implantable medical device according to any of the preceding Examples wherein the heterochelic component is present in an amount of about 0.01% to about 10% by weight of the coating.

In Example 11, the implantable medical device according to any of the preceding Examples wherein the homotelechelic polymer is present in an amount of about 90% to about 99% by weight of the coating.

In Example 12, a method of forming a coating on at least a portion of an implantable medical device includes applying a formulation having a heterochelic component, a homotelechelic polymer and a biocompatible initiator to at least a portion of a surface of the implantable medical device; and activating the biocompatible initiator to cross-link the heterochelic component and the homotelechelic polymer and form a coating on at least a portion of the surface of the implantable medical device. The heterochelic component includes a first reactive group and a second reactive group. The first reactive group is reactive with the portion of the surface and the second reactive group is non-reactive with the portion of the surface with which the first reactive group is reactive. The initiator reacts the homotelechelic polymer with the second reactive group of the heterochelic component.

In Example 13, the method according to any of the preceding Examples wherein activating the biocompatible initiator includes exposing the biocompatible initiator to UV light.

In Example 14, the method according to any of the preceding Examples wherein activating the biocompatible initiator includes exposing the biocompatible initiator to a temperature above room temperature.

In Example 15, the method according to any of the preceding Examples and further including storing the formulation comprising the heterochelic component, the homotelechelic polymer and the biocompatible initiator for more than 30 days before applying the formulation to at least a portion of the surface.

In Example 16, an implantable medical device includes a body member having a surface, and a lubricious coating applied to at least a portion of the surface. The coating includes a biocompatible initiator, an aprotic hydrophilic heterochelic component, and an aprotic hydrophilic homotelechelic polymer cross-linked with the heterochelic hydrophilic component. The aprotic hydrophilic heterochelic component includes a first reactive group and a second reactive group. The first reactive group is reactive with a portion of the surface and the second reactive group is non-reactive with the portion of the surface with which the first reactive group is reactive. The aprotic hydrophilic homotelechelic polymer is reactive with the second reactive group of the aprotic hydrophilic heterochelic component.

In Example 17, an implantable medical device according to any of the preceding Examples wherein the first reactive group is selected from the group consisting of isocyanate, isothiocyanate, orthosilicate esters, and chlorosilicates and combinations thereof.

In Example 18, an implantable medical device according to any of the preceding Examples wherein the first reactive group is isocyanate and the aprotic hydrophilic heterochelic component comprises at least one member selected from the group consisting of polyethylene glycol (PEG), polyvinylpyrrolidone (PVP), poly(ethylene glycol) monomethyl ether methacrylate (MPEGMA), poly(methyl vinyl ether), polyoxazolines, poly(N,N-dimethylacrylamide) and poly(N-vinylimidazole) and copolymers and mixtures thereof.

In Example 19, an implantable medical device according to any of the preceding Examples wherein the first reactive group is isocyanate and the aprotic hydrophilic heterochelic component comprises polyethylene glycol.

In Example 20, an implantable medical device according to any of the preceding Examples wherein the coating has a lower coefficient of friction than the surface on which it is applied.

In Example 21, an implantable medical device according to any of the preceding Examples wherein the biocompatible initiator is selected from the group consisting of photoinitiators and thermal initiators.

In Example 22, an implantable medical device according to any of the preceding Examples wherein the surface comprises a metal.

In Example 23, an implantable medical device according to any of the preceding Examples wherein the aprotic hydrophilic heterochelic component is present in an amount of about 0.01% to about 10% by weight of the lubricious coating.

In Example 24, an implantable medical device according to any of the preceding Examples wherein the aprotic hydrophilic homotelechelic polymer is present in an amount of about 90% to about 99.9% by weight of the lubricious coating.

In Example 25, an implantable medical device according to any of the preceding Examples wherein the aprotic hydrophilic homotelechelic polymer includes reactive groups of the same type as the second reactive group of the aprotic hydrophilic heterochelic component.

In Example 26, an implantable medical device according to any of the preceding Examples wherein the lubricious coating has a thickness from about 1 nanometer to about 1 millimeter.

In Example 27, a method of forming a coating on an implantable medical device, the method including applying a formulation including an aprotic hydrophilic heterochelic component, a hydrophilic homotelechelic polymer and a biocompatible initiator to at least a portion of a surface of the implantable medical device; activating the initiator; and cross-linking the aprotic hydrophilic heterochelic component and the hydrophilic homotelechelic polymer with the activated initiator to form a coating on at least a portion of the surface of the implantable medical lead. The aprotic hydrophilic heterochelic component includes a first reactive group and a second reactive group. The first reactive group is reactive with the portion of the surface and the second reactive group is non-reactive with the portion of the surface with which the first reactive group is reactive. The hydrophilic homotelechelic polymer is reactive with the second reactive group of the aprotic hydrophilic heterochelic component.

In Example 28, the method according to any of the preceding Examples wherein activating the initiator includes exposing the initiator to UV light.

In Example 29, the method according to any of the preceding Examples wherein activating the initiator includes exposing the initiator to an elevated temperature.

In Example 30, the method according to any of the preceding Examples wherein the aprotic hydrophilic heterochelic component is a polymer when the formulation is applied to at least a portion of the surface.

In Example 31, the method according to any of the preceding Examples and further including storing the formulation comprising the aprotic hydrophilic heterochelic component, the hydrophilic homotelechelic polymer and the biocompatible initiator for 30 days or longer.

In Example 32, the method according to any of the preceding Examples wherein the first reactive group is selected from the group consisting of isocyanate, isothiocyanate, orthosilicate esters, and chlorosilicates and combinations thereof.

In Example 33, the method according to any of the preceding Examples wherein the aprotic hydrophilic heterochelic component comprises at least one member selected from the group consisting of polyethylene glycol (PEG), polyvinylpyrrolidone (PVP), poly(ethylene glycol) monomethyl ether methacrylate (MPEGMA), poly(methyl vinyl ether), polyoxazolines, poly(N,N-dimethylacrylamide) and poly(N-vinylimidazole) and copolymers and mixtures thereof.

In Example 34, the method according to any of the preceding Examples wherein the aprotic hydrophilic heterochelic component is present in an amount of about 0.01% to about 10% by weight of the formulation.

In Example 35, the method according to any of the preceding Examples wherein the hydrophilic homotelechelic polymer is present in an amount of about 90% to about 99.9% by weight of the formulation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 shows an exemplary implantable medical device which can include embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention.

The detailed description of the invention which follows is intended to illustrate but not limit the invention.

In accordance with various embodiments of the disclosure, a lubricious coating may include a heterochelic component, a homotelechelic polymer and an initiator. As used herein, chelic refers to a component, such as a molecule, macromolecule or polymer, which provides coordination groups to form the structure of a compound. Telechelic refers to a component, such as a molecule, macromolecule or polymer, with reactive terminal groups that have the capacity to form intra-molecular as well as inter-molecular bonds. The prefix hetero means "different" while the prefix homo means "the same". For example, a heterochelic component is a component with two or more dissimilar reactive group, and a homotelechelic polymer is a polymer wherein the reactive groups are of the same type or have the same functionality.

The lubricious coating may be applied to any suitable substrate. Suitable substrates include metallic or metallic containing substrates, such as titanium, stainless steel and alloys thereof, and polymeric or polymeric containing substrates, such as polyolefins, polyesters, silicones, polyethers, urethanes and nylons. The lubricious coating may be applied to the entire substrate surface or to a portion of the substrate. In some embodiments, suitable substrates include implantable medical devices including but not limited to medical electrical devices, such as medical electrical leads. In some embodiments, the lubricious coating may reduce the coefficient of friction. For example, exemplary suitable substrates may include, but are not limited to, the following: o-rings, seals, fixation mechanisms (including an extendable/retractable fixation mechanism and its mechanical components), pulse generator housing, stents, or any other substrate having a surface where a lubricious coating or a reduction in the coefficient of friction is desired.

In certain embodiments, the lubricious coating is a one-step lubricious coating. For example, the heterochelic component, the homotelechelic polymer and the initiator may be combined and applied to a substrate. Following application, the initiator may be activated to polymerize the reactive groups of the heterochelic component and the homotelechelic polymer to form a cured or finished lubricious coating.

In some embodiments, the heterochelic component may be a molecule, such as a macromolecule or a small molecule. For example, the heterochelic component may be a small molecule having a molecular weight of less than about 900 Daltons. In some embodiments, the heterochelic component may be a combination or mixture of molecules.

In some embodiments, the heterochelic component may be macromolecule or a polymer. Polymers are molecules containing multiple repeating units (e.g., from about 5 to about 10 to about 25 to about 50 to about 100 to about 250 to about 500 to about 1000 or more repeating units) of one or more constitutional units, commonly referred to as monomers. For example, a polymer may contain from about 5 to about 1000 repeating unties, from about 10 to about 500 repeating unites, from about 25 to about 250 repeating unites, from about 10 to about 250 repeating units or from about 10 to about 50 repeating units. As used herein, the term "monomers" may refer to free monomers and to those that have been incorporated into polymers, with the distinction being clear from the context in which the term is used.

Polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

Where the heterochelic component is polymeric, the heterochelic component may include a first reactive group, a second reactive group and a backbone. The first and second reactive groups may be located at any suitable location along the backbone. In some embodiments, the backbone may be hydrophilic. For example, the backbone may be partially or completely soluble in water. Additionally or alternatively, the backbone may be aprotic. In some embodiments, the heterochelic component may be a copolymer and each monomer of the heterochelic component may be aprotic.

In some embodiments, the backbone of the heterochelic component may be non-reactive to the first and second reactive groups to prevent or reduce polymerization of the polymer chain with these groups. Thus, suitable polymers for the heterochelic component may vary depending on the reactive groups. In some embodiments, the first and second reactive groups may be located at any position along the backbone. For example, the first and second reactive groups may be end groups, side groups or a combination thereof.

Suitable backbones include, but are not limited to, polyethylene glycol (PEG), such as α-methacrylate ω-isocyanate PEG, polyvinylpyrrolidone (PVP), poly(ethylene glycol) monomethyl ether methacrylate (MPEGMA), poly(methyl vinyl ether), polyoxazolines, such as poly-2-methyl-2-oxazoline and poly-2-ethyl-2-oxazoline, poly(N,N-dimethylacrylamide) and poly(N-vinylimidazole) and combinations and copolymers thereof.

The heterochelic component includes two or more dissimilar reactive groups. That is, the heterochelic component includes at least a first reactive group and a second reactive group that are different or that are not the same. In some embodiments, the heterochelic component may contain more than one similar or same reactive group so long as the heterochelic component includes two or more dissimilar reactive groups. For example, the heterochelic component may include one or more first reactive groups and one or more second reactive groups. Reference will be made herein to a first reactive group and a second reactive group. However, it is understood that the heterochelic compound may include additional reactive groups and/or more than one first reactive group and/or second reactive group.

In some embodiments, the reactive groups of the heterochelic component may have orthogonal chemistries. For example, the first reactive group and the second reactive group may engage in different chemical reactions and/or may exhibit differences in their chemical reactivities.

In some embodiments, the first reactive group of the heterochelic component may be reactive towards the substrate on which the coating is applied. For example, in some embodiments, the first reactive group of the heterochelic component may covalently bond to the substrate. In some embodiments, the first reactive group may be aprotic or may be incapable of acting as a proton donor.

Suitable first reactive groups for the heterochelic component include, but are not limited to, isocyanate, isothiocyanate, orthosilicate esters, and chlorosilicates and combinations thereof.

In some embodiments, the second reactive group of the heterochelic component may be non-reactive towards to the substrate, the first reactive group of the heterochelic component or both the substrate and the first reactive group. In some embodiments, the second reactive group of the heterochelic component may react with the homotelechelic polymer in the presence of an activated initiator. For example, the second reactive group may be capable of participating in a controlled polymerization with the homotelechelic polymer. In some embodiments, suitable second reactive groups may be polymerizable by a free radical reaction, and may include, but are not limited to, acrylates, methacrylates, cyanoacrylates, vinyl ethers, vinyl esters, allyls and combinations thereof.

Suitable second reactive groups may also be polymerizable following a ring-opening polymerization, such as a cationic ring-opening polymerization (CROP), and may include, but are not limited to, epoxides, oxetanes, aziridines, β-butyrolactones and combinations thereof.

A suitable heterochelic component may include a mixture of different isomer molecules, such as a mixture of methylene diphenyl diisocyanate (MDI) isomers, with a low molecular weight chain extender.

The heterochelic component may be hydrophilic. For example, the heterochelic component may be hygroscopic or may exhibit diliquiscence. In some embodiments, the heterochelic component may be able to absorb many times its own weight in water. In some embodiments, the heterochelic component may be partially or completely soluble in water.

The heterochelic component may be aprotic. For example, the heterochelic component may be incapable of acting as a proton donor. In some embodiments, the heterochelic component may be a copolymer and each monomer is aprotic.

In certain embodiments, suitable amounts of heterochelic component in the lubricious coating include from about 0.01% to about 10% by weight of the lubricious coating, where the weight percent is calculated excluding the addition of solvents. Suitable amounts of the heterochelic component in the lubricious coating may also include from about 0.1% to about 5% by weight of the lubricious coating, where the weight percent is calculated excluding the addition of solvents.

The lubricious coating may also include a homotelechelic polymer having reactive groups of the same functionality. That is, the homotelechelic polymer may include only one type of reactive group. In some embodiments, the homotelechelic polymer may have more than one reactive group so long as all reactive groups are able to polymerize further following the same reaction mechanism.

In some embodiments, the homotelechelic polymer may be hydrophilic. For example, the homotelechelic polymer may be completely or partially soluble in water. Additionally or alternatively, the homotelechelic polymer may be aprotic. That is, the homotelechelic polymer may be unable to act as a proton donor.

As discussed herein, polymers are molecules containing a number of repeating units and may take on a number of configurations. Suitable configurations of the homotelechelic polymer include but are not limited to linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

The reactive groups of the homotelechelic polymer may be located at any position along the polymer. For example, a reactive group of the homotelechelic polymer may be an end group or a side group. The reactive groups of the homotelechelic polymer may be aprotic. That is, the reactive groups of the homotelechelic polymer may be unable to act as a proton donor.

In certain embodiments, suitable homotelechelic polymers include but are not limited to polyethylene glycol (PEG), such as α-methacrylate ω-isocyanate PEG, polyvinylpyrrolidone (PVP), poly(ethylene glycol) monomethyl ether methacrylate (MPEGMA), poly(methyl vinyl ether), polyoxazolines, such as poly-2-methyl-2-oxazoline and poly-2-ethyl-2-oxazoline, poly(N,N-dimethylacrylamide) and poly(N-vinylimidazole) and copolymers thereof.

The reactive groups of the homotelechelic polymer may be reactive with the second reactive group of the heterochelic component. In certain embodiments, the reactive groups of the homotelechelic polymer and the second reactive group of the heterochelic component may be reactive or polymerized in the presence of an activated initiator. The polymerization may, for example, form a continuous, cross-linked network between the heterochelic component and the homotelechelic polymer.

The reactive groups of the homotelechelic polymer may be capable of copolymerization with the second reactive group of the heterochelic component. In some embodiments, suitable reactive groups of the homotelechelic polymer may be the same as or similar to the reactive groups described as suitable for the second reactive group of the heterochelic component. In some embodiments, the reactive groups of the homotelechelic polymer may have the same chemistry or functionality as the second reactive group of the heterochelic component. For example, if the second reactive group of the heterochelic component is a polymerizable olefinic group, suitable reactive groups of the homotelechelic polymer may belong to the same category (e.g., acrylates, methacrylates, cyanoacrylates, vinyl ethers, vinyl esters, allyls, and/or combinations thereof.) In another example, where the second reactive group of the heterochelic component is an epoxy, a suitable homotelechelic polymer may be functionalized with an epoxy, an oxetane, an oxazoline, or other appropriate reactive groups capable of copolymerization through a cationic ring opening mechanism (e.g. aziridines, β-butyrolactones) and/or combinations thereof.

In certain embodiments, suitable amounts of homotelechelic polymer in the lubricious coating include from about 90% to about 99.9% by weight of the lubricious coating. Suitable amounts of the homotelechelic polymer in the lubricious coating may also include from about 93% to about 98% by weight of the lubricious coating.

The coating further includes at least one initiator. In some embodiments, the initiator may be a biocompatible initiator. In some embodiments, when activated, the initiator initiates polymerization of the heterochelic component and the homotelechelic polymer. Suitable biocompatible initiators include, for example, photoinitiators and thermal initiators which can be initiated upon exposure to light, such as UV light, or temperature, such as heat or an elevated temperature, such as above room temperature. In some embodiments, suitable biocompatible photoinitiators may include 1-[4-(2-hydroxyethoxy)-phenyl]-2-hydroxy-2-methyl-1-propane-1-one, such as Irgacure® 2959, 1-hydroxycyclohexyl-1-phenyl ketone, such as Irgacure® 184, and 2,2-dimethoxy-2-phenylacetophenone, such as Irgacure® 651, and combinations thereof. Irgacure® 2959, Irgacure® 184 and Irgacure® 651 are all available from Ciba Specialty Chemical. In some embodiments, suitable biocompatible thermal initiators may include (4-octyloxyphenyl)phenyliodonium hexafluoroantimonate, N-benzyl pyridinium bromide, and trimethoxy-[3-[4-(tetrahydrothiophen-1-ium-1-ylmethyl)phenoxy]propyl]silane bromide and combinations thereof.

Suitable biocompatible photoinitiators for cationic ring opening polymerization include but are not limited to, 4-bromophenyl)diphenylsulfonium triflate, (4-fluorophenyl) diphenylsulfonium triflate, (4-iodophenyl)diphenylsulfonium triflate, (4-methoxyphenyl)diphenylsulfonium triflate, (4-methylphenyl)diphenylsulfonium triflate, (4-methylthiophenyl)methyl phenyl sulfonium triflate, (4-phenoxyphenyl) diphenylsulfonium triflate, (4-phenylthiophenyl)diphenylsulfonium triflate, (4-tert-butylphenyl)diphenylsulfonium triflate, (cumene)cyclopentadienyliron(ii) hexafluorophosphate, (tert-butoxycarbonylmethoxynaphthyl)-diphenylsulfonium triflate, 1-naphthyl diphenylsulfonium triflate, 2-(4-methoxystyryl)-4,6-bis(trichloromethyl)-1,3,5-triazine, bis (4-tert-butylphenyl)iodonium perfluoro-1-butanesulfonate, bis(4-tert-butylphenyl)iodonium p-toluenesulfonate, bis(4-tert-butylphenyl)iodonium triflate, boc-methoxyphenyldiphenylsulfonium triflate, diphenyliodonium hexafluorophosphate, diphenyliodonium nitrate, diphenyliodonium perfluoro-1-butanesulfonate, diphenyliodonium p-toluenesulfonate, diphenyliodonium triflate, n-hydroxy-5-norbornene-2,3-dicarboximide perfluoro-1-butanesulfonate, n-hydroxynaphthalimide triflate, triarylsulfonium hexafluorophosphate salts, triphenylsulfonium perfluoro-1-butanesulfonate, triphenylsulfonium triflate, tris(4-tert-butylphenyl) sulfonium perfluoro-1-butanesulfonate, and tris(4-tert-butylphenyl)sulfonium triflate and combinations thereof.

Suitable biocompatible thermoinitiators for cationic ring opening polymerization include but are not limited to benzyl pyridinium salts and anilinium salts such as N-benzyl pyridinium bromide, N-benzyl o-cyano pyridinium bromide, N-benzyl p-cyanopyridinium bromide, N-benzyl N,N-dimethyl anilinium bromide, and benzyl triphenyl phosphonium bromide and combinations thereof. Onium salt cationic initiators may also be suitable thermoinitiators. That is, most of the cationic ring opening photoinitiators may also be thermally labile.

Suitable biocompatible photoinitiators for free-radical polymerization include but are not limited to acetophenones, benzils, benzoins, benzophenones, thioxanthones, 2-tert-butylanthraquinone, 9,10-phenanthrenequinone, camphorquinone, eosin Y, diphenyl(2,4,6-trimethylbenzoyl) phosphine oxide, phenylbis(2,4,6-trimethylbenzoyl) phosphine oxide, and sodium anthraquinone-2-sulfonate, and combinations thereof. Example acetophenones include 1-hydroxycyclohexyl phenyl ketone, 2,2-diethoxyacetophenone, 2,2-dimethoxy-2-phenylacetophenone, 2-benzyl-2-(dimethylamino)-4'-morpholinobutyrophenone, 2-hydroxy-2-methylpropiophenone, 2-hydroxy-4'-(2-hydroxyethoxy)-2-methylpropiophenone (such as Irgacure 2959), 2-methyl-4'-(methylthio)-2-morpholinopropiophenone, 3'-hydroxyacetophenone, 4'-ethoxyacetophenone, 4'-hydroxyacetophenone, 4'-phenoxyacetophenone, and 4'-tert-butyl-2',6'-dimethylacetophenone and combinations thereof. Example benzils and benzoins include 4,4'-dimethoxybenzoin, 4,4'-dimethylbenzil, benzoin, benzoin ethyl ether, and benzoin methyl ether and combinations thereof. Example benzophenones include 2-methylbenzophenone, 3,4-dimethylbenzophenone, 3-hydroxybenzophenone, 3-methylbenzophenone, 4-(diethylamino)benzophenone, 4-(dimethylamino)benzophenone, 4,4'-bis(diethylamino) benzophenone, 4,4'-bis[2-(1-propenyl)phenoxy] benzophenone, 4,4'-dihydroxybenzophenone, 4-benzoylbiphenyl 4-hydroxybenzophenone, 4-methylbenzophenone, benzophenone, benzophenone-3,3',4,4'-tetracarboxylic dianhydride, methyl benzoylformate, and Michler's ketone (4,4'-bis(N,N-dimethylamino)benzophenone) and combinations thereof. Suitable thiozanthones include but are not limited to 10-methylphenothiazine, 1-chloro-4-propoxy-9H-thioxanthen-9-one, 2,4-diethyl-9H-thioxanthen-9-one, 2-chlorothioxanthen-9-one, isopropyl-9H-thioxanthen-9-one, and thioxanthen-9-one, and combinations thereof.

Suitable biocompatible thermoinitiators for free-radical polymerization include but are not limited to diazenes (azo compounds), nitroxide-mediated polymerization initiators, and peroxides and combinations thereof. Suitable diazenes include but are not limited to 1,1'-azobis(cyclohexanecarbonitrile), 2,2'-azobis(2-methylpropionamidine) dihydrochloride, and 2,2'-azobis(2-methylpropionitrile) and combinations thereof. Suitable nitroxide-mediated polymerization initiators include but are not limited to N-tert-butyl-O-[1-[4-(chloromethyl)phenyl]ethyl]-N-(2-methyl-1-phenylpropyl)hydroxylamine, N-tert-butyl-N-(2-methyl-1-phenylpropyl)-O-(1-phenylethyl)hydroxylamine, (2,2,6,6-tetramethylpiperidin-1-yl)oxy (TEMPO), TEMPO methacrylate, and 2,2,5-trimethyl-4-phenyl-3-azahexane-3-nitroxide and combinations thereof. Suitable peroxide thermoinitiators include but are not limited to 1,1-bis(tert-amylperoxy)cyclohexane, 1,1-bis(tert-butylperoxy)-3,3,5-trimethylcyclohexane, 2,4-pentanedione peroxide, 2,5-bis(tert-butylperoxy)-2,5-dimethylhexane, 2,5-di(tert-butylperoxy)-2,5-dimethyl-3-hexyne, 2-butanone peroxide, benzoyl peroxide, cumene hydroperoxide, dicumyl peroxide, lauroyl peroxide, tert-butyl hydroperoxide, tert-butyl hydroperoxide, tert-butyl peracetate, tert-butyl peroxide, tert-butyl peroxybenzoate, and tert-butylperoxy 2-ethylhexyl carbonate and combinations thereof.

In certain embodiments, the lubricious coating may include one or more additional components. For example, the lubricious coating may include other functional moieties such as but not limited to anticoagulants, antimicrobials, growth factors for regulating cell behavior and combinations thereof.

In certain embodiments, the heterochelic component may be α-methacrylate ω-isocyanate PEG, the homotelechelic polymer may be methacrylate-PEG-methacrylate and the initiator may be 1-[4-(2-Hydroxyethoxy)-phenyl]-2-hydroxy-2-methyl-1-propane-1-one, such as Irgacure® 2959 available from Ciba Specialty Chemicals, Inc.

In certain embodiments, the lubricious coating may be applied on a surface of an implantable medical device, such as an interior or exterior surface of an implantable medical device. The lubricious property of the lubricious coating reduces the coefficient of friction of the surface of the implantable medical device. In certain embodiments, the lubricious coating may have a coefficient of friction of less than about 0.01. For example, the lubricious coating may have a coefficient of friction from about 0 to about 0.01 or from about 0 to about 0.05.

In certain embodiments, the lubricious coating is hydrophilic. For example, the lubricious coating may be partially or completely soluble in water. The water contact angle is one suitable method for determining the hydrophobicity of the lubricious coating. For example, a surface on which a smaller contact angle is formed between the surface and a fluid droplet is more hydrophilic than a surface having a larger contact angle. In some embodiments, the lubricious coating may be more hydrophilic than the surface of the surface of the implantable medical device on which it is applied. For example, the lubricious coating may have a smaller water contact angle than the surface of the implantable medical device on which it is applied.

In certain embodiments, the lubricious coating may be durable. A suitable method for measuring the durability of the lubricious coating includes subjecting the lubricious coating to a frictional force over a number of cycles. For example, a lubricious coating having suitable durability may suitably perform after subjected to 5 to 10 cycles of a frictional force.

In certain embodiments, the lubricious coating may be formed by mixing the heterochelic component, the homotelechelic polymer and the initiator to form a fluid or liquid formulation or mixture such as, but not limited to, a suspension or solution. In some embodiments, the components (e.g., the heterochelic component, the homotelechelic polymer and/or the initiator) do not chemically react until after the formulation is applied to the substrate. In other embodiments, one or more components may chemically react prior to applying the formulation to the substrate. For example, hydroxyl and/or amine-terminated heterochelic components may be reacted with MDI, which may make them surface active.

The formulation may be applied to a substrate on which the lubricious coating is desired. For example, the formulation may be applied to the surface of an implantable medical device. Suitable materials for the substrate include metallic materials such as gold, silver, titanium, stainless steel and alloys and mixtures thereof, and polymeric materials, including polyolefins, polyesters, silicones, polyethers, urethanes and nylons and mixtures thereof. Suitable materials also include combinations of metallic and polymeric materials.

In certain embodiments, the formulation may have shelf life of greater than 15, 30 or 45 days. For example, the formulation may be created and stored at room temperature for greater than 15, 30 or 45 days before use or application onto a substrate without significantly affecting the properties of the lubricious coating.

When applied to the substrate, the first reactive group of the heterochelic component may spontaneously react with the surface of the substrate. In some embodiments, for example, the first reactive group may covalently bond to the substrate. In some embodiments, the second reactive group of the heterochelic component may be non-reactive with the first reactive group of the heterochelic component and with the substrate. Similarly, in some embodiments, the homotelechelic polymer may be non-reactive with the first reactive group of the heterochelic component and the substrate.

After the formulation is applied to the substrate, the substrate may be subjected to conditions which trigger or activate the initiator. For example, the applied formulation may be exposed to UV light when the initiator is a photoinitiator, or the applied formulation may be exposed to an elevated temperature (e.g., above room temperature) when the initiator is a thermal initiator.

The activated initiator polymerizes the second reactive group of the heterochelic component and the homotelechelic polymer (e.g., the reactive groups of the homotelechelic polymer), forming a polymerized lubricious coating on the substrate. In some embodiments, the heterochelic polymer and the homotelechelic polymer may be polymerized to form a continuous, cross-linked network between the heterochelic component and homotelechelic polymer. In some embodiments, the cured formulation is a continuous, cross-linked network of hydrophilic polymer covalently bonded to the substrate.

In certain embodiments, the heterochelic component may include an isocyanate precursor, such as a hydroxyl group or an amine group. In such embodiments, the isocyanate precursor may be converted to an isocyanate prior to crosslinking the heterochelic component and the homotelechelic polymer. For example, the heterochelic component may be processed prior to being added to the formulation to convert the precursor to an isocyanate by treatment with a polyisocyanate reagent (e.g. poly(ethylene glycol) methacrylate may be converted to an isocyanate by allowing it to react with 2,4-toluenediisocyanate in situ.) Additionally or alternatively, the formulation may be processed prior to application onto the substrate to convert the precursor. Still further, the precursor may be processed after the formulation is applied to the substrate but before crosslinking the heterochelic component and the homotelechelic polymer.

In certain embodiments, the lubricious coating may be any suitable thickness such that the coating may be cured when exposed to the initiator conditions, such as UV light or heat. For example, the thickness of the lubricious coating may range from about 1 nanometer to about 10 millimeters and more particularly from about 0.1 micrometer to about 10 micrometers.

The lubricious coating may provide a platform for other functional moieties to be added to the surface of the substrate. For example, anticoagulants, antimicrobial and combinations thereof may be added to the surface of the lubricious coating. Additionally or alternatively, growth factors for regulating cell behavior, such as tissue ingrowth and endothelialization, may be added to the surface of the lubricious coating.

In certain embodiments, the lubricious coating is created by a one-step process in which the substrate can be primed and coated in the same step. As described herein, the heterochelic component of the lubricious coating may spontaneously react with the substrate and may function as a primer and a tie layer. In certain embodiments, the coating process does not require separate steps for priming and applying a coating, such as a hydrophilic polymer, on the substrate. Rather, the heterochelic component and the homotelechelic polymer are dispersed on the substrate simultaneously and the applied formulation is cured to form a lubricious coating.

In certain embodiments, the lubricious coating may be applied to one or more components of an implantable medical device, such as a medical electrical device or a catheter guidewire. The lubricious coating may be applied to the entire surface of an implantable medical device or a portion of the substrate surface. Medical electrical devices typically include (a) an electronic-signal-generating component and (b) one or more leads. The electronic-signal-generating component can contain a source of electrical power (e.g., a sealed battery) and an electronic circuitry package, which produces electrical signals that are sent into the body (e.g., the heart, nervous system, etc.). Leads comprise at least one flexible elongated conductive member (e.g., a wire, cable, etc.), which is insulated along at least a portion of its length, generally by an elongated polymeric component often referred to as a lead body. The conductive member is adapted to place the electronic-signal-generating component of the device in electrical communication with one or more electrodes, which provide for electrical connection with the body. Leads are thus able to conduct electrical signals to the body from the electronic-signal-generating component. Leads may also relay signals from the body to the electronic-signal-generating component.

Examples of medical electrical devices include, for example, implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others.

FIG. 1 is a schematic illustration of a lead system 100 for delivering and/or receiving electrical pulses or signals to stimulate, shock, and/or sense the heart 102. The lead system 100 includes a pulse generator 105 and a medical electrical lead 110. The pulse generator 105 includes a source of power as well as an electronic circuitry portion. The pulse generator 105 is a battery-powered device which generates a series of timed electrical discharges or pulses. The pulse generator 105 is generally implanted into a subcutaneous pocket made in the wall of the chest. Alternatively, the pulse generator 105 may be placed in a subcutaneous pocket made in the abdomen, or in another location. It should be noted that while the medical electrical lead 110 is illustrated for use with a heart 102, the medical electrical lead 110 is suitable for other forms of electrical stimulation/sensing as well.

The medical electrical lead 110 extends from a proximal end 112, where it is coupled with the pulse generator 105 to a distal end 114, which is coupled with a portion of a heart 102, when implanted or otherwise coupled therewith. An outer insulating lead body extends generally from the proximal end 112 to the distal end 114 of the medical electrical lead 110. Also disposed along a portion of the medical electrical lead 110, for example near the distal end 114 of the medical electrical lead 110, is at least one electrode 116 which electrically couples the medical electrical lead 110 with the heart 102. At least one electrical conductor (not shown) is disposed within the lead body and extends generally from the proximal end 112 to the distal end 114 of the medical electrical lead 110. The at least one electrical conductor electrically couples the electrode 116 with the proximal end 112 of the medical electrical lead 110. The electrical conductor carries electrical current and pulses between the pulse generator 105 and the electrode 116, and to and from the heart 102. In one option, the at least one electrical conductor is a coiled conductor. In another option, the at least one electrical conductor includes one or more cables. Typical lengths for such leads vary from about 35 cm to 40 cm to 50 cm to 60 cm to 70 cm to 80 cm to 90 cm to 100 cm to 110 cm to 120 cm, among other values. Typical lead diameters vary from about 1.0 to 1.3 to 1.5 to 1.7 to 1.9 to 2.0 to 2.1 to 2.3 to 2.5 to 2.7 to 2.9 to 3.0 mm, among other values.

In some embodiments, the lubricious coating may be applied to at least a portion of the exterior surface of the medical electrical lead 110 to reduce the coefficient of friction. The lubricious coating may be applied to any other component of lead system 100, including on surfaces exposed and surfaces not exposed to the outer environment (e.g., the patent environment), in which a reduced coefficient of friction is desirable.

In some embodiments, the lubricious coating may be applied to at least a portion of the pulse generator 105. For example, in some embodiments, the lubricious coating may be applied to the exterior surface of the can or housing of the pulse generator 105. Alternatively, the lubricious coating may be applied to any surface and may impart hydrophilic or lubricious properties.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device comprising:
 a body member having a surface; and
 a one-part lubricious coating layer applied to at least a portion of the surface, the one-part lubricious coating layer comprising the reaction products of:
 a biocompatible initiator;
 an aprotic hydrophilic heterochelic component; and
 an aprotic hydrophilic homotelechelic polymer cross-linked with the hydrophilic heterochelic component,
 wherein the aprotic hydrophilic heterochelic component is present in an amount of about 0.01% to about 10% by weight of the one-part lubricious coating layer and includes a first reactive group and a second reactive group, the first reactive group reactive with a portion of the surface and the second reactive group non-reactive with the portion of the surface with which the first reactive group is reactive, and
 wherein the aprotic hydrophilic homotelechelic polymer is present in an amount of about 90% to about 99.9% by weight of the one-part lubricious coating layer and is reactive with the second reactive group of the aprotic hydrophilic heterochelic component.

2. The implantable medical device of claim 1 wherein the first reactive group is selected from the group consisting of isocyanate, isothiocyanate, orthosilicate esters, and chlorosilicates and combinations thereof.

3. The implantable medical device of claim 1 wherein the first reactive group is isocyanate and the aprotic hydrophilic heterochelic component comprises at least one member selected from the group consisting of polyethylene glycol (PEG), polyvinylpyrrolidone (PVP), poly(ethylene glycol) monomethyl ether methacrylate (MPEGMA), poly(methyl vinyl ether), polyoxazolines, poly(N,N-dimethylacrylamide) and poly(N-vinylimidazole) and copolymers and mixtures thereof.

4. The implantable medical device of claim 1 wherein the first reactive group is isocyanate and the aprotic hydrophilic heterochelic component comprises polyethylene glycol.

5. The implantable medical device of claim 1 wherein the one-part lubricious coating layer has a lower coefficient of friction than the surface on which it is applied.

6. The implantable medical device of claim 1 wherein the biocompatible initiator is selected from the group consisting of photoinitiators and thermal initiators.

7. The implantable medical device of claim 1 wherein the surface comprises a metal.

8. The implantable medical device of claim 1 wherein the aprotic hydrophilic homotelechelic polymer comprises reactive groups of the same type as the second reactive group of the aprotic hydrophilic heterochelic component.

9. The implantable medical device of claim 1 wherein the one-part lubricious coating layer has a thickness from about 1 nanometer to about 1 millimeter.

10. A method of forming a single layer coating on an implantable medical device, the method comprising:
 applying a one-part lubricious composition comprising an aprotic hydrophilic heterochelic component, a hydrophilic homotelechelic polymer and a biocompatible initiator to at least a portion of a surface of the implantable medical device;

activating the initiator; and cross-linking the aprotic hydrophilic heterochelic component and the hydrophilic homotelechelic polymer with the activated initiator to form a coating on at least a portion of the surface of the implantable medical lead, wherein the aprotic hydrophilic heterochelic component is present in an amount of about 0.01% to about 10% by weight of the one-part lubricious coating composition formulation and comprises a first reactive group and a second reactive group, the first reactive group reactive with the portion of the surface and the second reactive group non-reactive with the portion of the surface with which the first reactive group is reactive, and wherein the hydrophilic homotelechelic polymer is present in an amount of about 90% to about 99.9% by weight of the one-part lubricious coating composition formulation and is reactive with the second reactive group of the aprotic hydrophilic heterochelic component.

11. The method of claim 10 wherein activating the initiator includes exposing the initiator to UV light.

12. The method of claim 10 wherein activating the initiator includes exposing the initiator to an elevated temperature.

13. The method of claim 10 wherein the aprotic hydrophilic heterochelic component is a polymer when the formulation is applied to at least a portion of the surface.

14. The method of claim 10 and further comprising storing the formulation comprising the aprotic hydrophilic heterochelic component, the hydrophilic homotelechelic polymer and the biocompatible initiator for 30 days or longer.

15. The method of claim 10 wherein the first reactive group is selected from the group consisting of isocyanate, isothiocyanate, orthosilicate esters, and chlorosilicates and combinations thereof.

16. The method of claim 10 wherein the aprotic hydrophilic heterochelic component comprises at least one member selected from the group consisting of polyethylene glycol (PEG), polyvinylpyrrolidone (PVP), poly(ethylene glycol) monomethyl ether methacrylate (MPEGMA), poly(methyl vinyl ether), polyoxazolines, poly(N,N-dimethylacrylamide) and poly(N-vinylimidazole) and copolymers and mixtures thereof.

* * * * *